(12) United States Patent
Bach et al.

(10) Patent No.: US 8,960,188 B2
(45) Date of Patent: Feb. 24, 2015

(54) NEBULIZER

(75) Inventors: Alexander Bach, Essen (DE); Jens Besseler, Bingen am Rhein (DE); Holger Holakovsky, Witten (DE); Manuel Krakowka, Welver (DE); Gilbert Wuttke, Dortmund (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 511 days.

(21) Appl. No.: 12/952,488

(22) Filed: Nov. 23, 2010

(65) Prior Publication Data

US 2011/0290243 A1 Dec. 1, 2011

(30) Foreign Application Priority Data

Nov. 25, 2009 (EP) .................................... 09014681

(51) Int. Cl.
*A61M 11/00* (2006.01)
*B67B 1/00* (2006.01)
*A61M 15/00* (2006.01)
*B05B 11/00* (2006.01)

(52) U.S. Cl.
CPC ....... *A61M 15/0065* (2013.01); *A61M 15/0036* (2014.02); *A61M 15/007* (2014.02); *A61M 15/0081* (2014.02); *A61M 2205/276* (2013.01); *B05B 11/309* (2013.01)
USPC ............. 128/200.21; 128/200.14; 222/153.09

(58) Field of Classification Search
CPC .......... A61M 15/0065; A61M 15/007; A61M 15/0081; A61M 2205/27; A61M 2205/273; B05B 11/309
USPC .......................... 128/200.21, 200.19, 203.21, 128/200.14–200.23; 604/68–72, 257, 262, 604/275, 279; 222/153.09; 215/315, 311, 215/307, 223; 220/368, 367.1; 239/359–361
See application file for complete search history.

(56) References Cited

U.S. PATENT DOCUMENTS

| 5,394,866 A | 3/1995 | Ritson et al. |
| 6,988,496 B1 | 1/2006 | Eicher et al. |
| 7,665,461 B2 * | 2/2010 | Zierenberg et al. ...... 128/200.21 |
| 8,656,910 B2 * | 2/2014 | Boeck et al. ............. 128/200.21 |
| 2007/0062518 A1 * | 3/2007 | Geser et al. ............. 128/200.14 |

(Continued)

FOREIGN PATENT DOCUMENTS

| WO | 2005080002 A1 | 9/2005 |
| WO | 2006125577 A2 | 11/2006 |

OTHER PUBLICATIONS

"activate." Collins English Dictionary. 2000. http://search.credoreference.com/content/entry/hcengdict/activate/0 (Jun. 12, 2014).*

(Continued)

*Primary Examiner* — Tan-Uyen (Jackie) T Ho
*Assistant Examiner* — Mark K Han
(74) *Attorney, Agent, or Firm* — Michael P. Morris; Mary-Ellen M. Devlin

(57) ABSTRACT

A nebulizer includes an insertable container and a securing mechanism for holding the container in the nebulizer such that the container can move back and forth but can not be separated. The securing mechanism is formed by a metal unitary part. The securing mechanism forms a transportation lock for holding the container unmovable in the housing in a delivery state of the nebulizer. The securing mechanism forms a cage which encompasses the container.

22 Claims, 12 Drawing Sheets

(56) References Cited

U.S. PATENT DOCUMENTS

Figure 1:
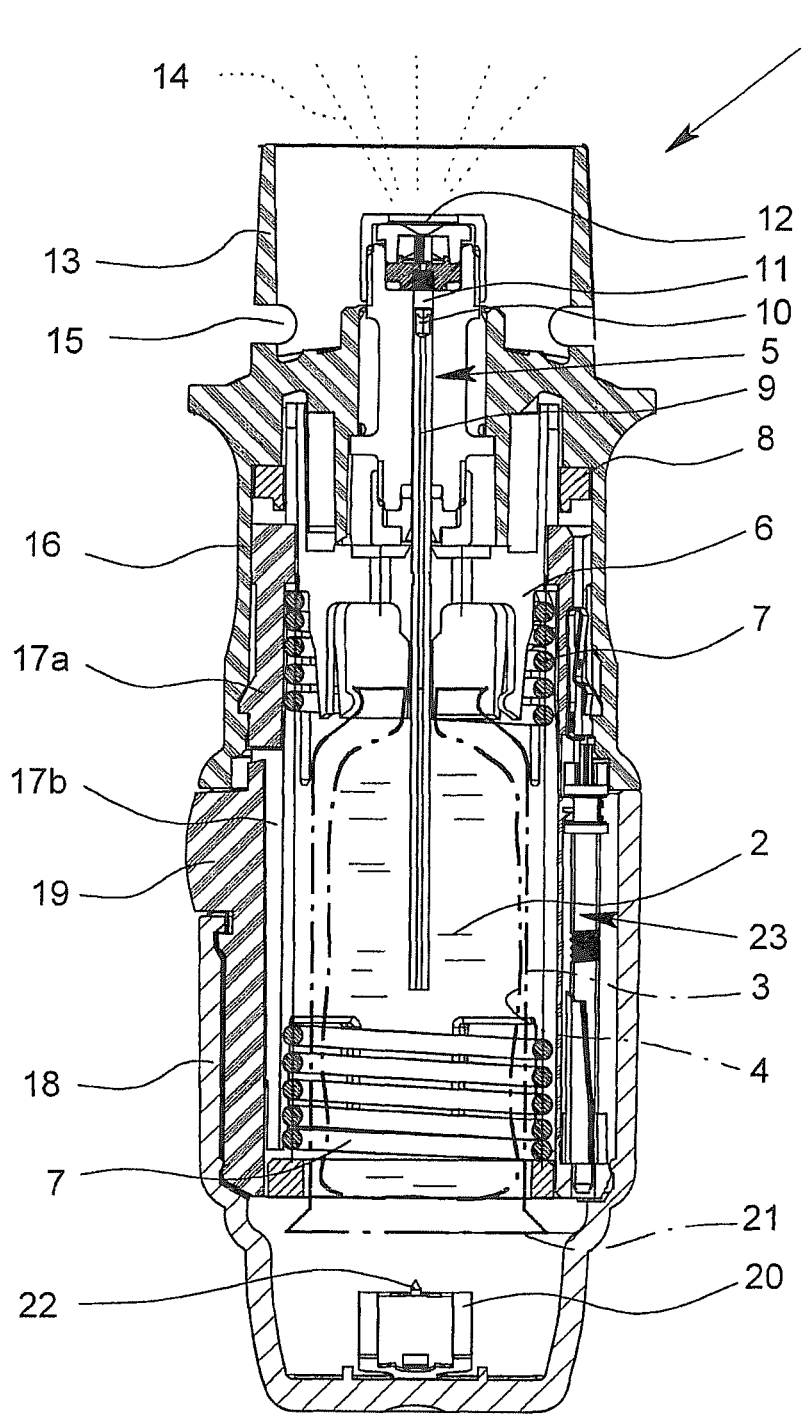

2007/0107720 A1\* 5/2007 Boeck et al. ............. 128/200.21
2008/0083408 A1\* 4/2008 Hodson et al. ........... 128/200.23
2008/0249459 A1 10/2008 Godfrey et al.
2010/0084531 A1\* 4/2010 Schuchman ............... 248/311.2

OTHER PUBLICATIONS

International Search Report and Written Opinion for PCT/EP2010/067901, mailed Apr. 14, 2011.

\* cited by examiner

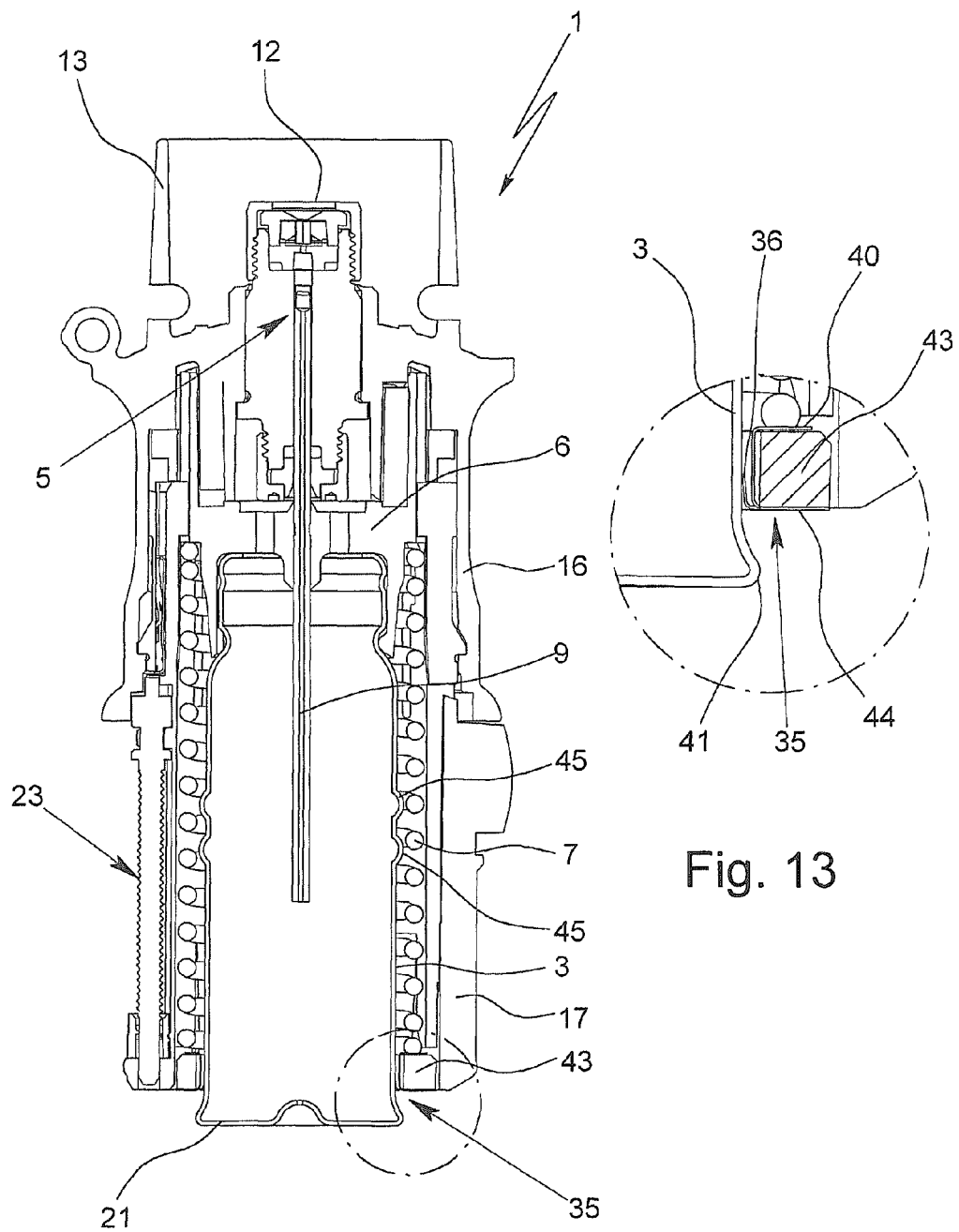

NEBULIZER

The present invention relates to a nebulizer for dispensing a fluid.

One starting point for the present invention is a nebulizer illustrated in WO 2006/125577 A2. The nebulizer comprises, as a reservoir for fluid which is to be atomized or nebulized, an insertable rigid container having an inner bag containing the fluid and a pressure generator with a drive spring for delivering and atomizing the fluid. Preferably, the container is secured against removal. For the purpose, the nebulizer of its housing may be designed such that it can not be opened after the container has been inserted.

Preferably, the container is pre-installed in nebulizer in the delivery state. In particular, the pre-installed container is held by a transportation lock unmovable within the housing in the delivery state in order to avoid any undesired opening of the container.

Before being used for the first time the nebulizer is completely closed. Thus, the preinstalled container is opened by a delivery tube piercing a sealing and a septum to fluidically connect to the inner bag of the container. Further, the transportation lock is opened so that the container can move inside the nebulizer back and forth.

By rotating the lower housing part of the nebulizer the drive spring can be put under tension and fluid can be sucked into a compression chamber of the pressure generator. Simultaneously, the container is moved into the lower housing part in a stroke movement within the nebulizer and when tensioned for the first time the container may be pierced through its base by a piercing element in the lower housing part to allow venting of the container. After manual operation of a locking element the drive spring is released and the fluid in the pressure chamber is put under pressure by the drive spring and is delivered or atomized through a nozzle into a mouthpiece as an aerosol, without the use of propellant gas.

WO 2007/022898 A2 discloses a similar nebulizer. A container can be inserted into a housing of the nebulizer. The housing is closed by a lower or bottom housing part. The container is moving axially forth and back during conveying of the fluid to be nebulized, during pressure generation and/or during nebulization. A counter can be arranged in the housing part. The counter locks the nebulizer against further use if a predetermined number of operations has been reached or exceeded. Then, the housing part may be replaced together with the counter and the container. The container may be connected inseparably with the housing part. However, WO 2007/022898 A2 does not describe a simple and inexpensive construction for connecting the container with the housing part inseparably and such that the container is moveable back and forth within the housing during conveying of the fluid, pressure generation and/or nebulization.

Object of the present invention is to provide a nebulizer with optimized handling and/or simple assembly or construction, even with pre-installed container.

The above object is achieved by a nebulizer as described herein. Preferred embodiments are also described herein.

The nebulizer comprises a securing means for holding the container in the housing or a housing part thereof inseparably, wherein the container is moveable back and forth within the housing during conveying of fluid, pressure generation and/or nebulization. This allows opening of the nebulizer and simultaneously prevents separation of the container from the housing or housing part of the nebulizer.

According to a first aspect of the present invention, the securing means comprises or consists of a metal and/or stamping part. This allows a simple construction and, in particular, integration of the securing means into current designs.

According to a second aspect of the present invention, the securing means consists of a single unitary part. This allows a very simple and inexpensive construction.

According to a third aspect of the present invention, the securing means does not only connect the container inseparably with the housing or housing part such that the container is moveable back and forth within the housing during conveying of the fluid, pressure generation and/or nebulization, but also forms in a transportation lock which holds the container unmoveably in the housing in a delivery state, in particular with the pre-installed container being still closed. This facilitates assembly and avoids any undesired opening of the container in the delivery state. Further, the multiple functions of the securing means simplify construction.

Additionally or alternatively the securing means may comprise an opening means for opening a venting hole of the container. This additional function simplifies the construction as well.

According to a fourth aspect of the present invention, the nebulizer or housing comprises a cage as securing means for holding the container such that the container is moveable back and forth, but is inseparable from the housing or a housing part thereof, and/or such that the container is unmoveably held in a delivery state of the nebulizer. This allows a simple construction. In particular, the cage is ideal for allowing a limited moveability of the container relative to the housing or housing part and simultaneously connecting the container inseparably with the housing or housing part. This allows a very simple and inexpensive construction.

Preferably the nebulizer has the still closed container provided therein and the nebulizer is constructed so that the container is opened inside the nebulizer before or during the first use of the nebulizer. This basic idea is hereinafter called also "pre-installed container". This makes operation easy as there is no need to open the nebulizer, insert the container and close the nebulizer. Moreover, undesirable soiling or damage to the nebulizer caused by incorrect handling when inserting the container can thus be prevented. Accordingly, there is better operational safety as it is impossible for the container to be wrongly inserted or otherwise misused during insertion.

The different aspects of the present invention mentioned above and described in the following can be realized independently from each other and in any combination.

Figure 2:
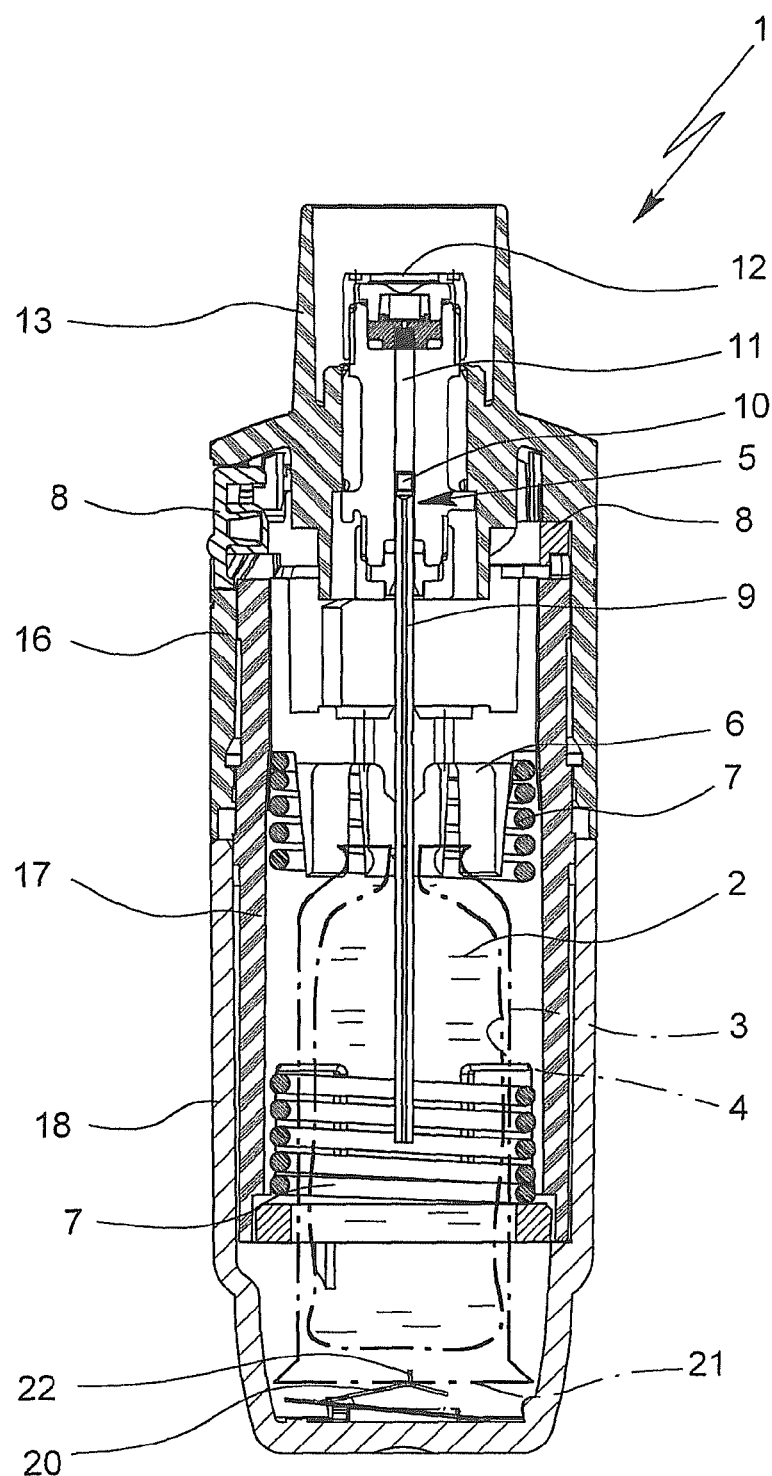
Figure 3:
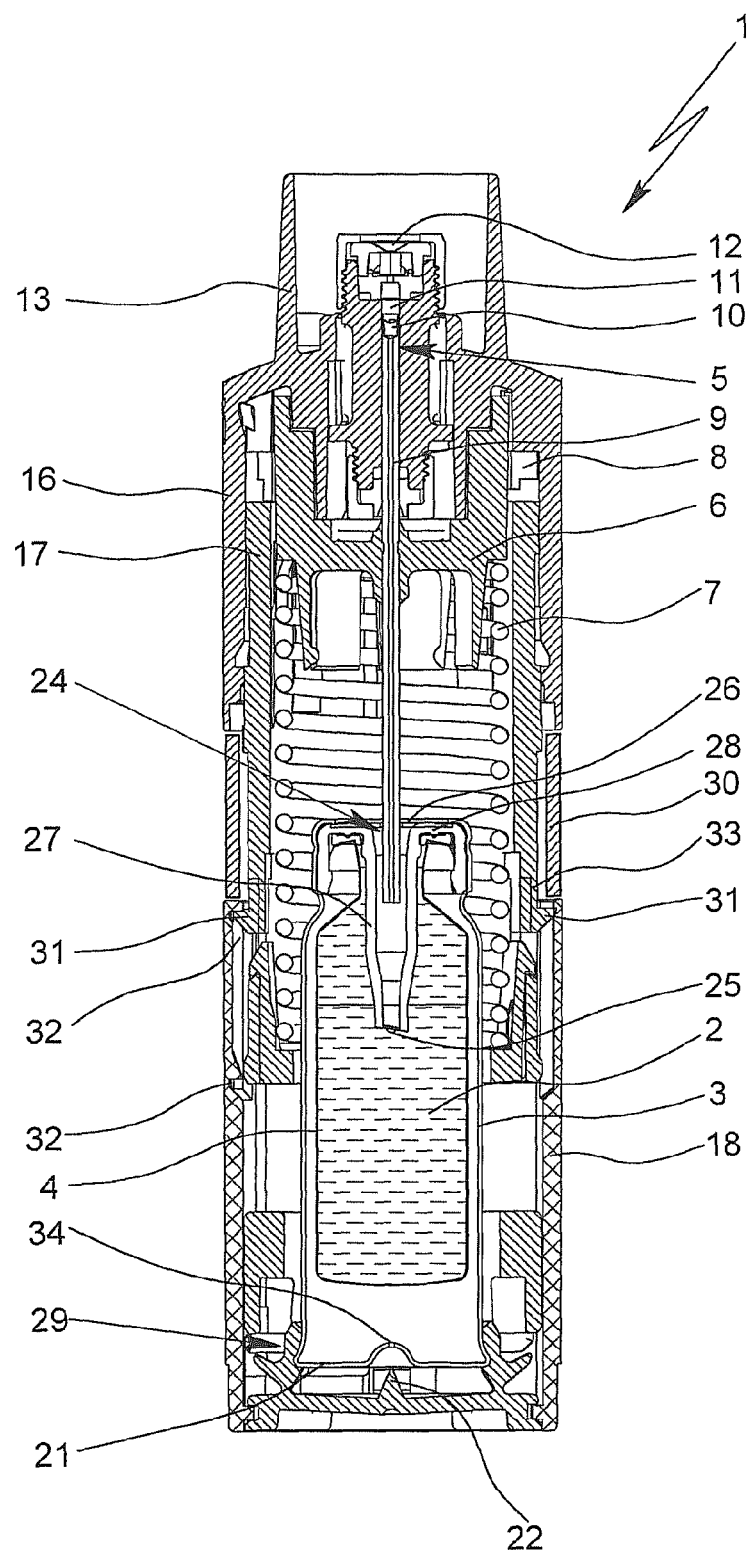
Figure 4:
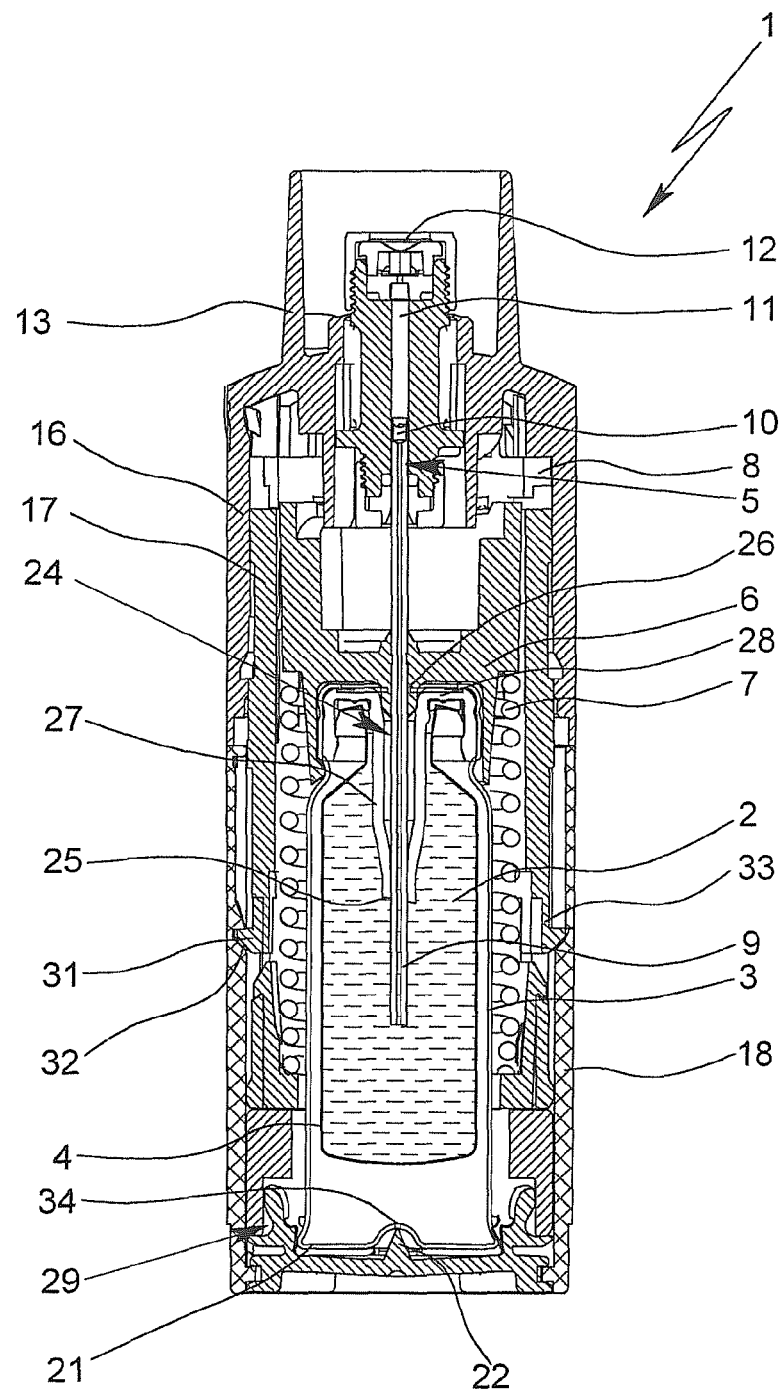
Figure 5:
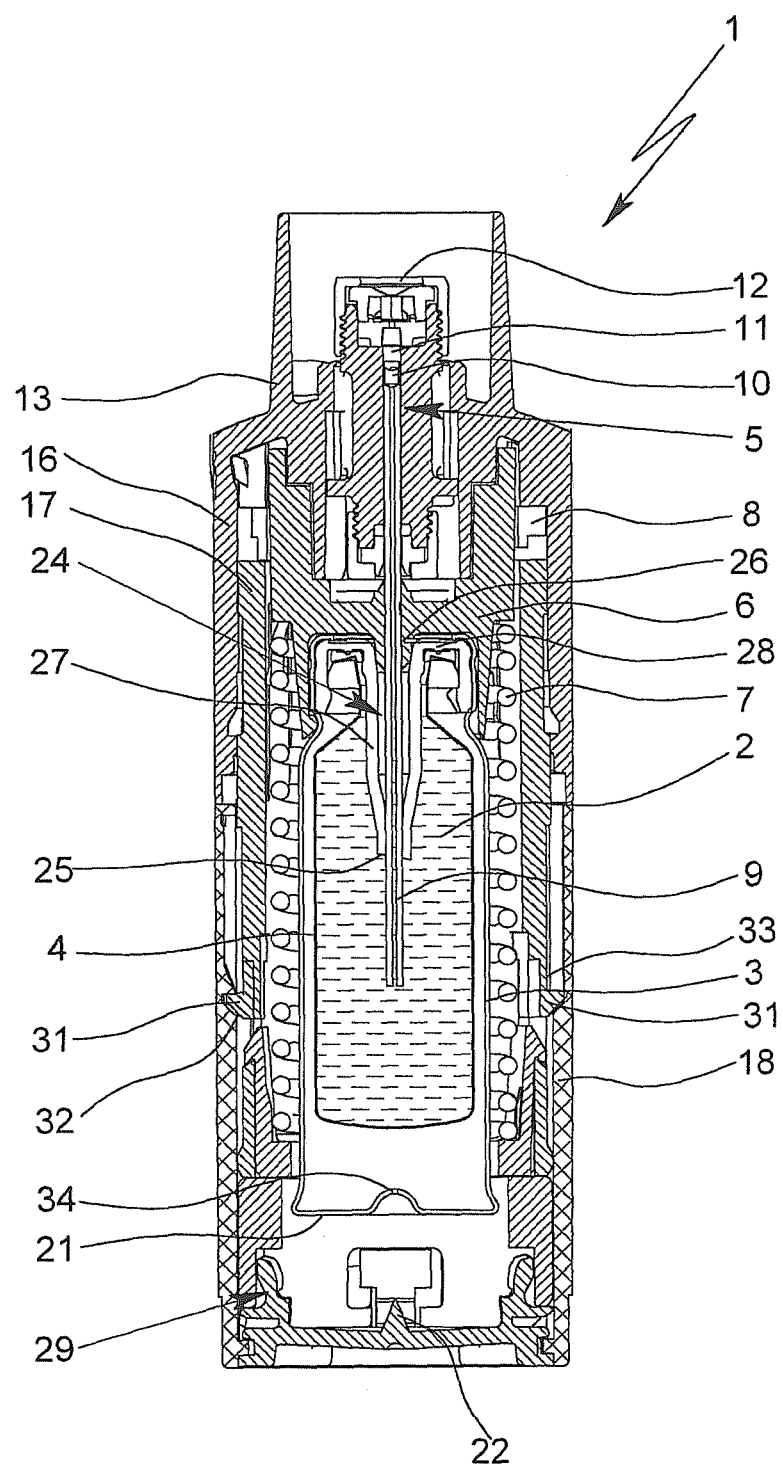
Figure 6:
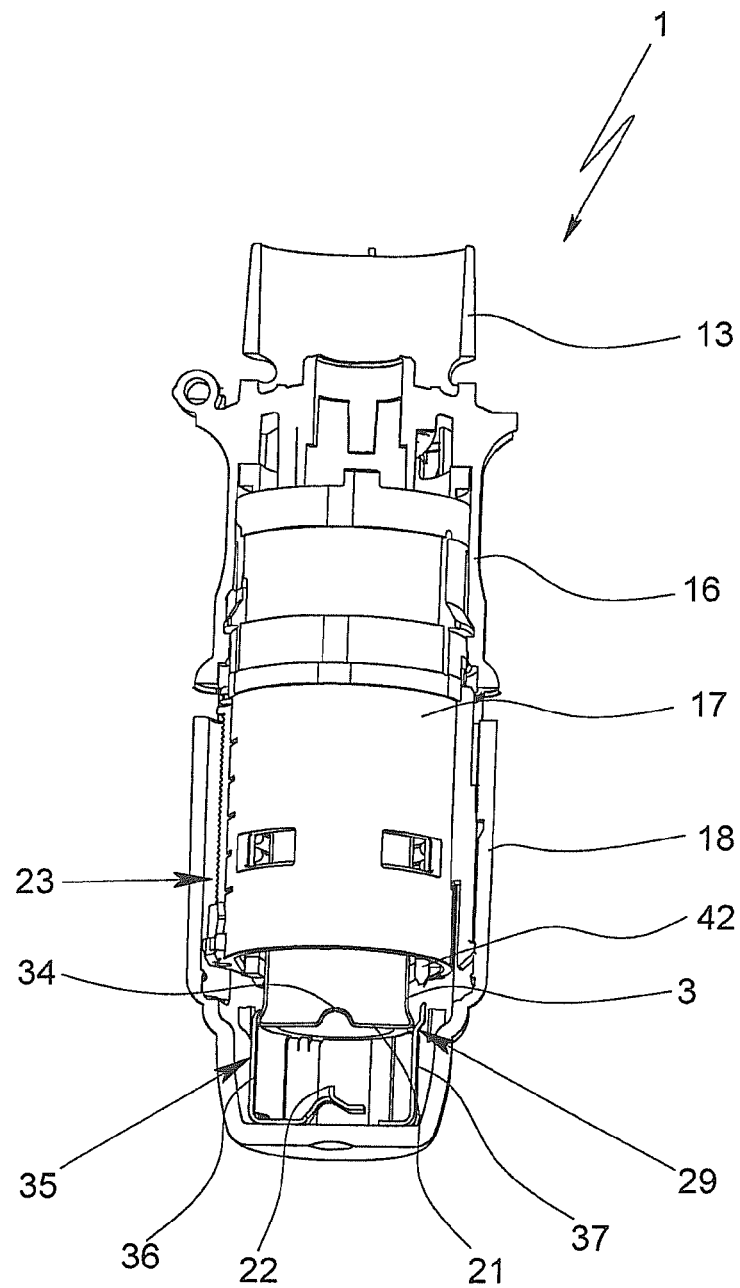
Figure 7:
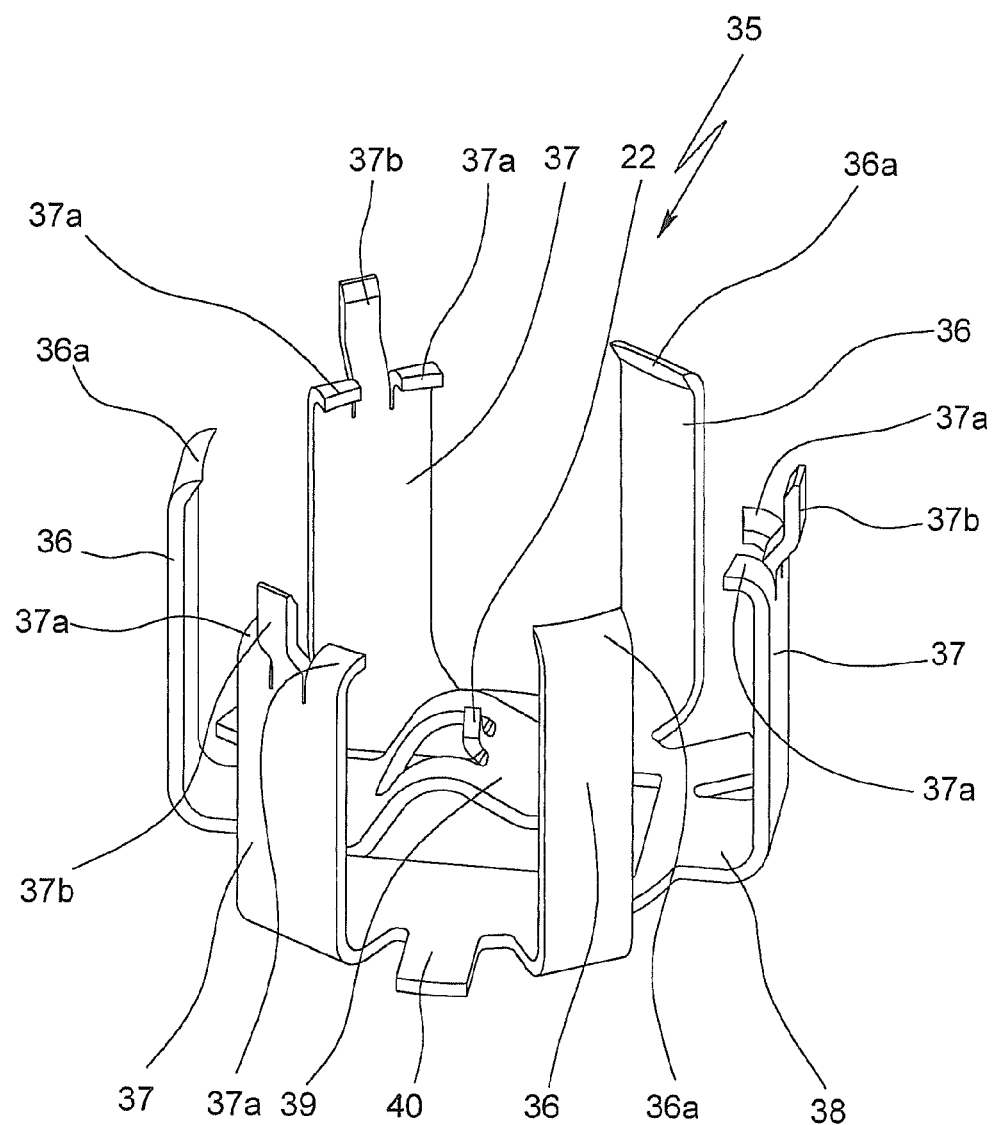
Figure 8:
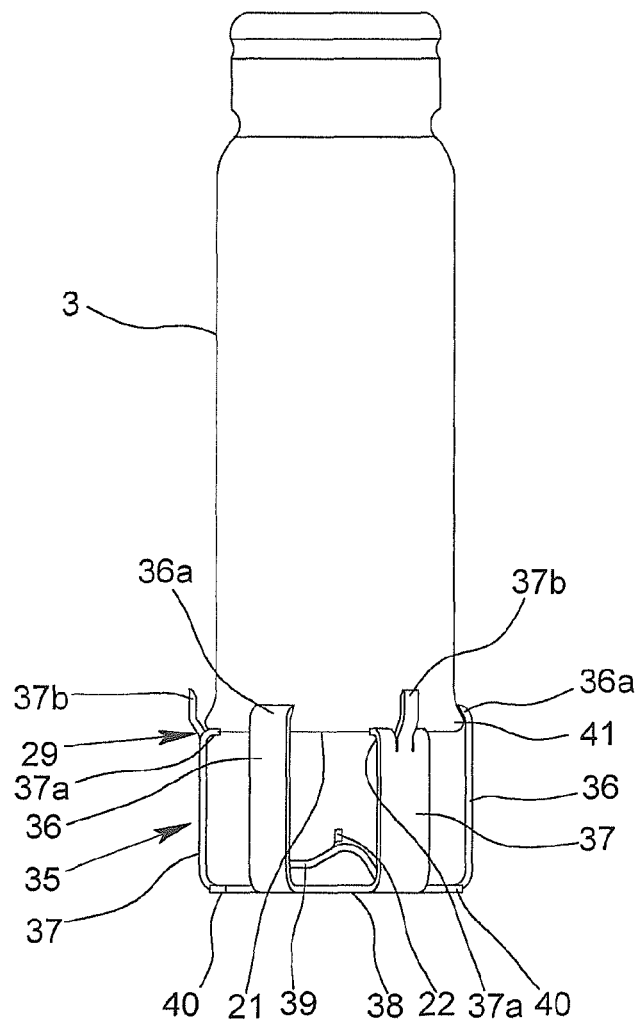
Figure 9:
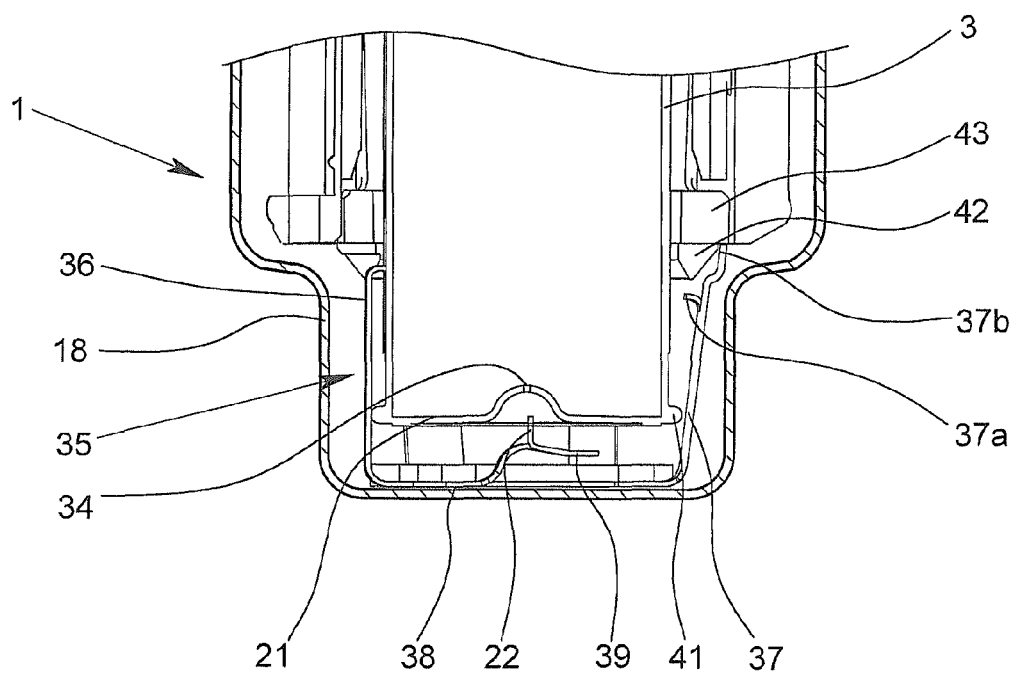
Figure 10:
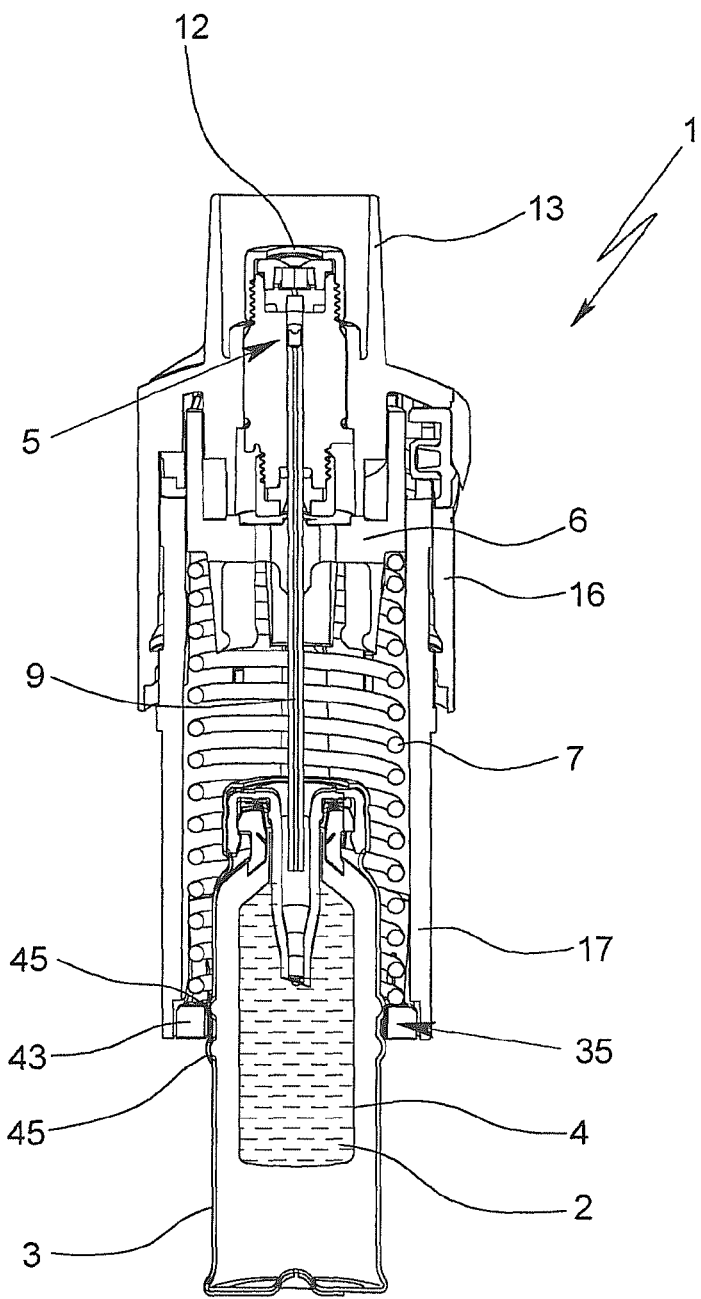
Figure 11:
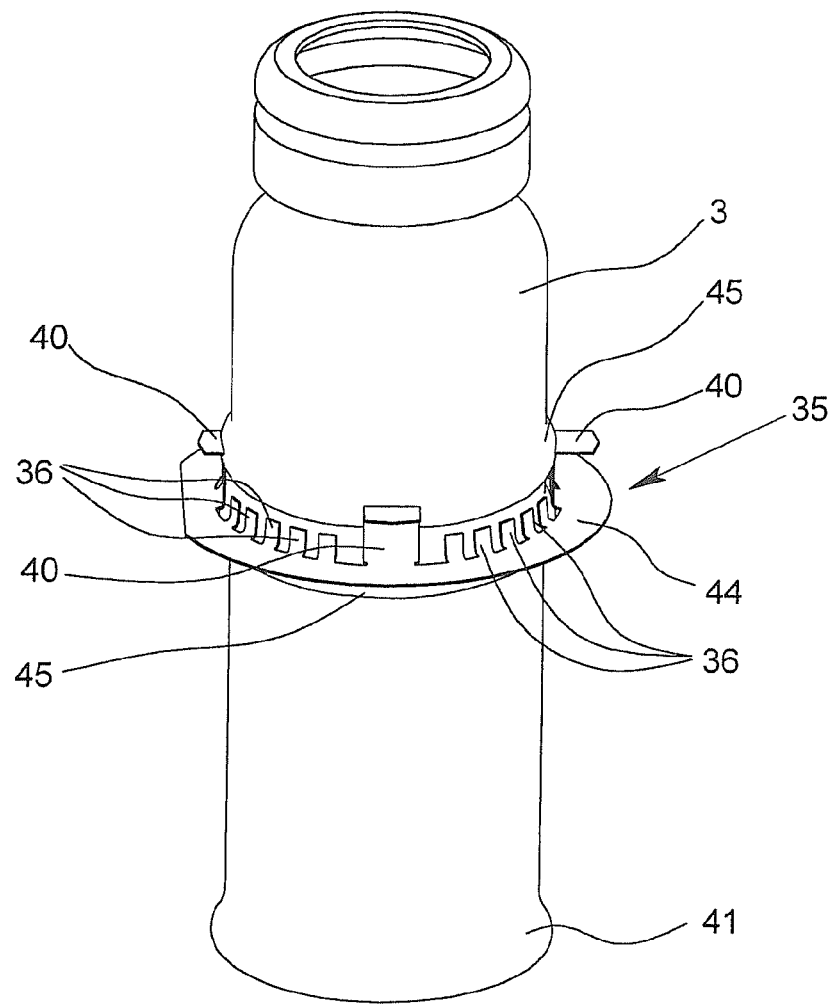

Further advantages, features, characteristics and aspects of the present invention will become apparent from the claims and the following description of preferred embodiments with reference to the drawings. It shows:

FIG. 1 a schematic section of a known nebulizer in a non-tensioned state;

FIG. 2 a schematic section, rotated through 90° compared with FIG. 1, of the known nebulizer in a tensioned state;

FIG. 3 a schematic section of a nebulizer in a delivery state with a partly closed housing and with a pre-installed, closed container;

FIG. 4 a schematic section of the nebulizer according to FIG. 3 in an activated, tensioned state with the completely closed housing and with the opened container;

FIG. 5 a schematic section of the nebulizer according to FIG. 4 in a non-tensioned state;

FIG. 6 a schematic section of a nebulizer according to a first embodiment of the present invention with a partly closed housing and with a securing means in a housing part holding unmoveably a container in the nebulizer;

FIG. 7 a perspective view of the securing means;

FIG. 8 a side view of the securing means holding the associated container unmoveably;

FIG. 9 a schematic partial view of a part of the nebulizer with opened securing means so that the container can move;

FIG. 10 a schematic section of a nebulizer according to a second embodiment of the present invention in a delivery state without lower housing part;

FIG. 11 a perspective view of the container of the nebulizer according to FIG. 10 with an associated securing means;

FIG. 12 a schematic section of the nebulizer according to FIG. 10 in the activated, non-tensioned state; and FIG. 13 a partial enlarged view of FIG. 12.

In the Figures, the same reference numerals have been used for identical or similar parts, resulting in corresponding or comparable properties and advantages, even if the associated description is not repeated.

FIGS. 1 and 2 show a known nebulizer 1 for atomizing a fluid 2, particularly a highly effective pharmaceutical composition or the like, diagrammatically shown in a non-tensioned state (FIG. 1) and in a tensioned state (FIG. 2). The nebulizer 1 is constructed in particular as a portable inhaler and preferably operates only mechanical and/or without propellant gas.

When the fluid 2, preferably a liquid, more particularly a pharmaceutical composition, is nebulized, an aerosol 14 (FIG. 1) is formed, which can be breathed in or inhaled by a user. Usually the inhaling is done at least once a day, more particularly several times a day, preferably at set intervals, depending on the complain or illness from which the patient is suffering.

The nebulizer 1 is provided with or comprises an insertable container 3 containing the fluid 2. The container 3 thus forms a reservoir for the fluid 2 which is to be nebulized. Preferably, the container 3 contains an amount of fluid 2 or active substance which is sufficient to provide up to 200 dosage units, for example, i.e. to allow up to 200 sprays or applications. A typical container 3, as disclosed in WO 96/06011 A1, holds e.g. a volume of about 2 to 10 ml.

The container 3 is substantially cylindrical or cartridge-shaped and once the nebulizer 1 has been opened the container can be inserted therein from below and changed if desired. It is preferably of rigid construction, the fluid 2 in particular being held in a collapsible bag 4 in the container 3.

The nebulizer 1 comprises preferably a pressure generator 5 for conveying and nebulizing the fluid 2, particularly in a preset and optionally adjustable dosage amount. The pressure generator 5 comprises preferably a holder 6 for the container 3, an associated drive spring 7, only partly shown, a locking element 8 which can be manually operated to release the spring 7, a conveying element, such as a conveying tube 9, a non-return valve 10, a pressure chamber 11 and/or an nozzle 12 for nebulizing the fluid 2 into a mouthpiece 13. The container 3 is fixed or held in the nebulizer 1 via the holder 6 such that the conveying tube 9 penetrates into the container 3. The holder 6 may be constructed so that the container 3 can be exchanged.

As the drive spring 7 is axially tensioned the holder 6 with the container 3 and the conveying tube 9 is moved downwards in the drawings and fluid 2 is sucked out of the container 3 into the pressure chamber 11 of the pressure generator 5 through the non-return valve 10 (conveying of the fluid 2, suction stroke). Then, the nebulizer 1 is in the so-called activated or tensioned state.

During the subsequent relaxation after actuation of the locking element 8 the fluid 2 in the pressure chamber 11 is put under pressure as the conveying tube 9 with its now closed non-return valve 10 is moved back upwards by the relaxation of the drive spring 7 and now acts as a pressing ram or piston (pressure generation and/or nebulization). This pressure forces the fluid 2 through the nozzle 12, whereupon it is nebulized into the aerosol 14, as shown in FIG. 1.

Generally, the nebulizer 1 operates with a spring pressure of 5 to 200 MPa, preferably 10 to 100 MPa on the fluid 2, with a volume of fluid 2 delivered per stroke of 10 to 50 μl, preferably 10 to 20 p. 1, most preferably about 15 μl. The fluid 2 is converted into or nebulized as aerosol 14 the droplets of which have an aerodynamic diameter of up to 20 μm, preferably 3 to 10 μm. Preferably, the generated jet spray has an angle of 20° to 160°, preferably 80° to 100°. These values also apply to the nebulizer 1 according to the teaching of the present invention as particularly preferred values.

A user (not shown) can inhale the aerosol 14, while an air supply can be sucked into the mouthpiece 13 through at least one air supply opening 15.

Preferably, the nebulizer 1 can be manually activated or tensioned. The nebulizer 1 comprises preferably an upper housing part 16 and an inner part 17 which is rotatable relative thereto (FIG. 2) having an upper part 17*a* and a lower part 17*b* (FIG. 1), while an in particular manually operable (lower) housing part 18 is releasable fixed, particularly fitted onto the inner part 17, preferably by means of a retaining element 19. Preferably, the housing parts 16 and 18 form a housing of the nebulizer 1. In order to insert and/or replace the container 3 the housing part 18 can be detached from the nebulizer 1 or its housing.

The housing part 18 can be rotated relative to the upper housing part 16, carrying with it the part 17*b* of the inner part 17. As a result the drive spring 7 is tensioned in the axial direction by means of a gear or transmission (not shown) acting on the holder 6. During tensioning the container 3 is moved axially downwards until the container 3 assumes an end position as shown in FIG. 2. In this activated or tensioned state the drive spring 7 is under tension. During the nebulizing process the container 3 is moved back into its original position (non-tensioned position or state shown in FIG. 1) by the drive spring 7. Thus the container 3 executes a lifting or stroke movement during the tensioning process and during the atomizing process.

The housing part 18 preferably forms a cap-like lower housing part and fits around or over a lower free end portion of the container 3. As the drive spring 7 is tensioned the container 3 moves with its end portion (further) into the housing part 18 or towards the end face thereof, while an aeration means, such as an axially acting spring 20 arranged in the housing part 18, comes in contact with base 21 of the container 3 and pierces the container 3 or a base seal thereon with a piercing element 22 when the container 3 makes contact with it for the first time, to allow air in or aeration.

The nebulizer 1 may comprise a monitoring device 23 which counts the actuations of the nebulizer 1, preferably by detecting the rotation of the inner part 17 relative to the upper part 16 of the housing. Preferably, the monitoring device 23 blocks the actuation or use of the nebulizer 1, e.g. blocks the actuation of the locking element 8, when a certain number of actuations or discharged doses has been reached or exceeded.

A preferred construction and mode of the inhaler or nebulizer 1 will now be described in more detail with reference to FIGS. 3 to 5, but emphasizing only essential differences from the nebulizer 1 according to FIGS. 1 and 2. The remarks relating to FIGS. 1 and 2 thus apply preferably accordingly or in a similar manner, while any desired combinations of features of the nebulizer 1 according to FIGS. 1 and 2 and the nebulizer 1 described below are possible.

FIGS. 3 to 5 show, in schematic sectional views, a nebulizer 1 according to a preferred embodiment of the present invention. FIG. 3 shows the nebulizer 1 in a delivery state, i.e. with pre-installed container 3 which is still closed. In this state, the housing of the nebulizer 1 is not completely closed, in particular the housing part 18 is not completely pushed on the inner part 17. FIGS. 4 and 5 show the nebulizer 1 in an activated and/or tensioned state with the housing completely closed and with the container 3 opened. In FIG. 4, the nebulizer 1 or drive spring 7 is tensioned, i.e. the container 3 is in its lower position. FIG. 5 shows the nebulizer 1 in a non-tensioned state, e.g. after the delivery or discharge of one dose of the fluid 2; the container 3 is in its upper position.

The container 3 is already mounted or pre-installed in the nebulizer 1 in the delivery state, as shown in FIG. 3. In this state, the container 3 is still closed, i.e. there is no fluidic connection between the container 3 or its bag 4 on one hand and the nebulizer 1 or its pressure generator 5 or the conveying element on the other hand.

The container 3 comprises a fluid outlet 24 for outputting the fluid 2 to be dispensed. In particular, the fluid outlet 24 allows a fluidic connection between the container 3 or its bag 4 on one hand and the nebulizer 1, its pressure generator 5 or the conveying element on the other hand.

The fluid outlet 24 has an inner closure 25 that is preferably formed by a septum, a membrane, a plastic seal or the like and/or is provided inside the container 3. Optionally, a second or outer closure 26 can be provided.

Preferably, the closures 25 and 26 are designed such that successive opening is possible by means of one common element, in particular the conveying element or conveying tube 9 or the like, and/or by piercing.

In the preferred embodiment, the first closure 25 and second closure 26 are arranged one after the other and/or spaced in axial direction or direction of the stroke movement of the container 3 or with respect to the main outlet direction of the fluid 2.

Generally, the container 3, fluid outlet 24 or closures 25 or 26 are opened in particular by means of a conveying element, such as the conveying tube 9, or the like and/or by piercing or in any other suitable manner. In particular, the opening is achieved by moving the container 3 relative to the nebulizer 1 or conveying element or tube 9 or the like and/or by movement in longitudinal or axial direction.

Preferably, the first or inner closure 25 is formed or supported by a closure part 27 extending from the outlet or head end of the container 3 into the container 3 or bag 4. The second or outer closure 26 is preferably located adjacent to the head or axial end of the container 3 and/or held or connected to a flange 28, which can be formed by the closure part 27 or any other suitable part. However, other constructional solutions are possible.

In the delivery state according to FIG. 3, the container 3 has been pre-installed, i.e. inserted into the nebulizer 1. However, the container 3 or its fluid outlet 24 is not yet opened. In particular, the second closure 26 is already opened, but not the first closure 25. This is achieved in particular in that the housing of the nebulizer 1 is closed only partly, i.e. not completely, in the delivery state, preferably by not completely closing or pushing on the housing part 18 in the shown embodiment. Preferably, the housing part 18 is snapped on or inserted only partly in the delivery state.

In particular, the container 3 is attached to or held by or secured in the housing part 18, in particular by a transportation lock 29, which is preferably arranged within or at the housing part 18. The transportation lock 29 holds the container 3 preferably temporarily, in particular before attaching the housing part 18 to the nebulizer 1 and/or in the delivery state. In particular, the transportation lock 29 holds the container 3 fixed during the fluidic connection of container 3 and/or during the mechanic connection of container 3, here with holder 6. Preferably, the transportation lock 29 holds the container 3 fixed during opening, in particular piercing, the container 3.

In the delivery state, in which the nebulizer 1 can be shipped or delivered to the user or is still packed, the nebulizer 1 or the housing part 18 is preferably secured, in particular by means of a securing member 30, such that the container 3 and/or housing part 18 are held sufficiently spaced from the nebulizer 1 or upper housing part 16 and/or prevented from being completely inserted or pushed on the conveying element or tube 9, the housing or inner housing part 17 or the like and/or such that (complete) opening of the container 3, namely of the first closure 25, is prevented.

In the shown embodiment, the securing member 30 is preferably mounted between the housing part 18 and the upper housing part 16 and preferably engages with or between the housing parts 16 and 18, so that the housing part or lower part 18 is axially secured or is kept or held sufficiently away or spaced from the upper housing part 16 to be able to hold the (still) closed container 3 or first closure 25 away from the conveying tube 9.

In the preferred embodiment, the securing member 30 is at least substantially hollow and/or cylindrical and is disposed axially between the (lower) housing part 18 and the upper housing part 16. To activate the nebulizer 1 or prepare its for use, i.e. to push the housing part 18 fully on in the axial direction and thereby open the container 3, the securing member 30 first has to be removed or released or opened. In the shown preferred embodiment, the securing member 30 is constructed in the manner of a banderole or the like, made of plastics, for example, and/or can be manually opened, removed or destroyed. The securing member 30 may alternatively or simultaneously form or constitute a seal of origin. However, other embodiments of the securing member 30 are also possible, e.g. in the form of a security tag or the like.

Preferably, the container 3 and/or housing part 18 are held positively or in a form-fit or interlocking manner in the delivery state. This is achieved in the preferred embodiment in particular by means of the transportation lock 29 acting between the container 3 and the housing part 18, and the securing member 30 acting between the housing part 18 and the housing of the nebulizer 1 or the upper housing part 16 or the like. However, the transportation lock 29 or securing member 30 could also act directly between the container 3 on one hand and the nebulizer 1, its housing, the upper housing part 16, the inner housing part 17 or the holder 6 on the other hand.

In the non-activated position, the housing part 18 is preferably secured so that it cannot be lost and, in particular, cannot be released. Then, the housing or lower part 18 of the nebulizer 1 can no longer be detached from the nebulizer 1 after it has been (partially) axially pushed on for the first time, i.e. the nebulizer 1 cannot be opened any longer, with the result that that the container 3 cannot be changed, i.e. cannot be removed again.

In order to secure the housing part 18, it is preferably held or latched positively or in an interlocking or form-fit manner. Preferably, the housing part 18 is secured by means of at least one latching lug 31, protrusion, nose or the like which engages in an associated latching recess 32 in the housing part 18 or the like and, thereby, secures the housing part 18 against axial removal by interlocking engagement. In the present embodiment, the latching lug 31 may be formed by or at a latching arm 33 which can preferably flex. Thus, a ratchet-like means for securing the housing part 18 to the nebulizer 1 or its housing or the upper housing part 16 is formed. However, other constructional solutions are also possible.

Once the security member 30 has been removed a user (not shown) can push the housing part 18 fully on in the axial direction and thereby open the container 3, i.e. first closure 25, by inserting the conveying element or conveying tube 9. FIGS. 4 and 5 show this activated state with the housing part 18 pushed fully on and/or the container 3 open (fluidically connected to the nebulizer 1 or its pressure generator 5 or the conveying element or tube 9). In this pushed on or activated state, the housing part 18 is preferably secured or axially fixed again by interlocking engagement, i.e. form-fit manner in axial direction, particularly by the engagement of the latching arm 33 or latching lug 31 in a corresponding further latching recess 32 or by means of some other mechanical securing device.

FIG. 4 shows the nebulizer 1 or container 3 in the activated state, the container 3, i.e. first closure 25, is open, i.e. the container 3 or its fluid 2 is fluidically connected to the nebulizer 1 or its pressure generator 5, and the housing part 18 has been pushed fully on in the axial direction. In order to bring the holder 6 into (complete) engagement with the container 3 at the head end and then be able to move the container 3 back and/or forth for the suction/tensioning and pressing strokes, it may be necessary to tension the nebulizer 1 or it drive spring 7 for the first time. During this tensioning process the holder 6 is moved together with the conveying tube 9 axially towards or into the housing part 18, thus bringing the holder 6 into (complete) engagement with the container 3 and preferably also moving or pressing the container 3 against the piercing element 22 in the region of the base of the housing part 18 and thereby piercing or opening a venting hole 34 in the container base 21. FIG. 4 shows the nebulizer 1 in this tensioned and activated state. The holder 6 is engaged with the container 3 and the conveying tube 9 has been fully inserted into the container 3.

FIG. 5 shows the nebulizer 1 in the relaxed, non-tensioned state, i.e. after atomization or discharge of a dose of the fluid 2. The holder 6 and the container 3 are in the upper position. The holder 6 is still engaged with the container 3 and remains engaged during the further uses of the nebulizer 1. Further, the container 3 is still open and fluidically connected, i.e. the nebulizer 1 remains activated.

The nebulizer 1 is activated after the removal of the securing member 30 and (total) axial pushing on of the housing part 18 and can be used in the same way as the nebulizer 1 shown in FIGS. 1 and 2. The pre-installation of the container 3 prevents the wrong container 3 or used containers 3 from being inserted in the nebulizer 1 by the user.

As preferably the container 3 cannot then be removed, especially because the nebulizer 1 cannot be opened and the housing part 18 cannot be removed again, undesirable replacement of the container 3 by the user and in particular undesirable interim or subsequent opening of the nebulizer 1 by the user can be prevented.

To prevent unwanted opening of the container 3, particularly of the first closure 25, in the delivery state of the nebulizer 1, preferably the transportation lock 29 is provided. By frictional, forcible or interlocking engagement, for example, the transportation lock 29 prevents the container 3 from undesirably moving axially in the nebulizer 1, e.g. during transportation, in the event of accidental dropping of the nebulizer 1 or the like.

Preferably, the opening of the transportation lock 29 occurs automatically when closing the nebulizer 1 or its housing completely, i.e. when snapping or pushing on the housing part 18 completely towards the upper housing part 16. During this (axial or telescopic) closing movement, the transportation lock 29 is opened and the container 3 released in axial direction preferably only in a last part of the movement and/or just little before the final completely closed position is reached or just when the final completely closed position is reached.

The closing movement of the nebulizer 1 opens the transportation lock 29 preferably automatically. In particular, the transportation lock 29 is opened by the direct or indirect interaction with or actuation by the housing of the nebulizer 1, the inner part 17 or its lower part 17b, a holding ring 38 bearing the spring 7 or the like. Preferably, the container 3 and/or first closure 25 are opened as well as the transportation lock 29 by means of a common actuation, here the closing movement of the nebulizer 1 or its housing or bottom part 18.

FIGS. 4 and 5 show the transportation lock 29 in the open position, i.e. wherein the container 3 is free to move axially.

Preferably, in the non-activated state, i.e. when the housing part 18 has not been pushed on fully, the nebulizer 1 may be locked to prevent tensioning of the pressure generator 5, i.e. in particular to prevent rotation of the inner part 17 relative to the upper housing part 16. This may be important when the nebulizer 1 is supplied in the delivery state with the pressure generator 5 not under tension. Accordingly, the inhaler 1 may have a barrier, so that the inner part 17 can only be rotated relative to the upper housing part 16 when the housing part 18 has been pushed fully on. Alternatively or additionally, the securing member 30 may block not only pushing on of the bottom part 18 in the delivery state, but also any rotation of the inner part 17 until the securing member 30 has been opened, released or removed.

In the following, a first embodiment of the inhaler or nebulizer 1 according to the present invention will be described in detail with reference to FIGS. 6 to 9, wherein only essential differences will be emphasized so that the previous remarks and explications relating to the nebulizers 1 according to FIGS. 1 to 5 apply preferably in a corresponding or similar manner.

FIG. 6 shows in a very schematic, partially sectional view the nebulizer 1 according to the first embodiment of the present invention. The nebulizer 1 is shown a transitional state from the delivery state to the activated state with not completely closed housing or housing part 18. The housing part 18 has already been pushed on the inner part 17 more than initially provided in the delivery state such as shown in FIG. 3. Therefore, the container 3 has already been opened in the state shown in FIG. 6. Further, the securing member 30, which preferably secures the housing part 18 in the delivery state against pushing on the inner part 17, has already been released or opened or removed in the state shown in FIG. 6.

The nebulizer 1 or its housing comprises a securing means 35 for holding the container 3 such that the container 3 is moveable back and forth for the conveying of the fluid 2, pressure generation and/or nebulization, but is inseparable from the housing or housing part 18, and/or such that the container 3 is unmoveably held in the delivery state of the nebulizer 1.

The securing means 35 is located or arranged preferably at or in the housing part 18 as shown in FIG. 6.

FIG. 7 shows in a perspective view a preferred embodiment of the securing means 35. FIG. 8 shows the securing means 35 connected with the container 3.

Preferably, the securing means 35 comprises or consists of a metal and/or stamping part and/or consists of a single, unitary part as shown in FIG. 7.

Preferably, the securing means 35 is made of steel, in particular spring steel.

Preferably, the securing means 35 is produced from sheet material by cutting, stamping or the like and/or by bending.

Preferably, the securing means 35 or the part forms a cage, in particular, encompasses the container 3 or an end portion thereof.

Preferably, the securing means 35 comprises holding elements 36 and/or locking elements 37. The elements 36 and 37 are preferably designed like arms, fingers leaves or the like. In particular, the elements 36, 37 are alternately distributed over a circumference of the container 3 and/or extend at least essentially axially or in the direction of the back and forth movement of the container 3.

Preferably, the elements 36 and 37 are held by or connected with a base 38 of the securing means 35.

Preferably, the securing means 35 or base 38 comprises or holds the piercing element 22 for piercing the container 3, i.e. opening the container base 21 or its venting hole 34 in the activated and tensioned state, i.e. when the container 3 reaches its lower end position. In the shown embodiment, the piercing element 22 is formed by a respective bending of a spring portion 39 of the securing means 35 or its base 38. The spring portion 39 can support or facilitate the (complete or final) connection of the container 3 to holder 6.

The securing means 35 or base 38 comprises preferably at least one or multiple fixing portions 40 for fixing the securing means 35 at or in the nebulizer 1 or housing or housing part 18. In particular, the fixing portions 40 may fix the securing means 35 when the securing means 35 is pressed into the housing part 18 by cooperating with the side wall of the housing part 18. However, it is also possible to overmold the securing means 35, its base 38, the fixing portions 40 or the like. Moreover, the securing means 35 could be connected with the housing part 18 or the like in any other suitable manner.

Preferably, the securing means 35 does not only prevent the separation of the container 3 from the nebulizer 1, its housing or housing part 18, but also forms the transportation lock 29 for holding the container 3 unmovable in the housing in the delivery state of the nebulizer 1. FIGS. 6 and 8 shows this state or situation when the container 3 is held (axially) unmovable by the securing means 35, i.e. when the transportation lock 29 is closed. In this situation, the container 3 or its preferably radially protruding end or edge 41 of the container 3 is held between the holding element 36 and locking element 37, in particular between respectively formed or bent ends of the elements 36 and 37.

In the shown embodiment, the container end or edge 41 is caught between end portions 36a and 37a of the elements 36 and 37. The holding elements 36 grip or extend over the edge 41 and the locking elements 37 or its end portions 37a grip or extend under the edge 41 or container base 21 so that the edge 41 and container 3 are securely held preventing any axial movement of the container 3 relative to the securing means 35 and relative to the associated housing part 18 in this state, i.e. with locked securing means 35/transportation lock 29.

The holding element 36 and the locking elements 37 are distributed alternatingly around the container 3 or edge 41.

Preferably, the end portions 36a of the holding elements 36 end in a first radial plane and the end portions 37a of the locking elements 37 end in another, second radial plane, wherein the two planes are axially offset to hold the edge 41 in between and/or wherein the second plane is located axially between the first plane and the lower end position of the container 3 or the lower end of the housing part 18 or the piercing element 22. Additionally or alternatively, the end portions 36a end on another radius (outer radius) than the end portions 37a and/or are axially spaced therefrom.

The end portions 36a and/or 37a are preferably form like claws or the like and/or extend preferably radially inwardly.

Preferably, the elements 36 and/or 37 can flex with its free ends radially outwardly.

For example, the ends of the end portions 36a may be inclined such that the container 3 may be inserted into or connected with the securing means 35 by a respective axial force so that the holding elements 36 flex outwardly to allow passing of edge 41. However, the holding elements 36 can be flexed outwardly also by a suitable tool (not shown) or the like when the container 3 is inserted, in particular with its edge 41, into the securing means 35.

Preferably, the holding elements 36 prevent separation of the container 3 from the securing means 35 and, thus, from the associated housing part 18 or the like.

The locking elements 37 or its end portions 37a can be flexed radially outwardly in order to open the axial holding or transportation lock 29 (this will be explained in detail with reference to FIG. 9 in the following). Then, the container 3 can axially move, in particular back and forth and/or with its edge 41 between the first plane and the piercing element 22 in the present embodiment.

In the present embodiment, the locking elements 37 comprise actuation portions 37b (preferably formed at the free ends and/or between adjacent end portions 37a). Preferably, the actuation portions 37b form axial extensions which may be radially offset. The actuation portion 37b cooperate with an associated control member 42 or multiple control members 42 of the nebulizer 1 such that the locking elements 37 are flexed radially outwardly when (completely) closing the housing to open the transportation lock 29 (here primarily formed by the locking elements 37 or its end portions 37a).

FIG. 6 shows schematically the control member 42 axially spaced from the associated actuation portion 37b as the housing has not yet been closed (completely).

FIG. 9 shows a lower part of the completely closed nebulizer 1 with opened transportation lock 29, i.e. with radially outwardly flexed locking elements 37. FIG. 9 shows that the control member 42 has an inclined guiding surface or the like to convert the axial closing movement into the radial opening movement of the actuation portion 37b and, thus, of the associated locking element 37 to open the transportation lock 29, in particular when the housing has been completely closed or when the housing part 18 has been pushed completely on the nebulizer 1.

The control member 42 is preferably formed as an axial protrusion. It can be formed by or at a ring 43 or any other bearing means of the nebulizer 1 for counter-bearing the drive spring 7 in the inner part 17 or by or at any other suitable component if the nebulizer such as the inner part 17.

The control member 42 may be formed like an axial protruding ring or shoulder or ridge which extends along the ring 43.

The control member 42 may additionally secure the holding elements 36 against axial opening when the housing is completely closed as schematically shown in FIG. 9. In this case, the control member 42 contacts the holding element(s) 36 or its end portions 36a peripherally on the outer side to prevent any outward flexing. Then, the securing means 35 or its holding elements 36 are secured against opening so that the container 3 is securely held within the securing means 35 or the cage formed by the securing means 35 or holding elements 36.

FIG. 9 shows the container 3 in its lower position when the piercing element 22 can pierce the venting hole 34 or an associated seal attached to the container base 21.

In the present embodiment, the securing means 35 has multiple functions. It holds the container 3 (in the activated state/with completely closed housing) such that it can move back and forth, in particular during conveying of the fluid 2, during pressure generation and/or during nebulization, wherein the container 3 is inseparable from the housing or the housing part 18. Further, the securing means 35 forms the transportation lock 29 and/or holds the container 3 unmovable in the delivery state of the nebulizer 1. Additionally or alternatively, the securing means 35 comprises an opening means, here the piercing element 22, for opening the venting hole 34 of the container 3.

Preferably, the securing means 35 forms a cage which cannot be separated from the container 3 after connecting it with the container 3.

The transportation lock 29 and the locking elements 37 are kept opened during the normal use of the nebulizer 1, in particular as long as the housing is (completely) closed. When the housing is opened, i.e. the housing part 18 is detached, the control member 42 may disengage from the actuation portions 37b so that the locking element 37 can close or flex inwardly again. Then, the locking elements 37 may grip with its end portions 37a over the edge 41 of the container 3 such that an additional lock is formed which prevents that the container 3 can be separated from the securing means 35/housing part 18.

The securing means 35 prevents separation of the container 3 from the housing part 18. Therefore, the container 3 can be replaced or exchanged only together with the housing part 18 if the housing part 18 can be detached from the nebulizer 1 or inner part 17 at all. However, it is also possible that the nebulizer 1 can not be opened. Then, the container 3 can not be replaced.

In the following, a second embodiment of the nebulizer 1 and the securing means 35 will be described with reference to FIGS. 10 to 13. The previous remarks and explications apply in a corresponding or similar manner. Only essential differences or new aspects of the second embodiment will be explained.

FIG. 10 shows in a schematic sectional section the nebulizer 1 according to the second embodiment in the delivery state. The housing part 18 is omitted.

In the second embodiment, the securing means 35 is arranged or located at or within the non-detachable part of the housing of the nebulizer 1, in particular at or in the upper housing part 16 or inner part 17. In particular, the securing means 35 is located or mounted at or within the ring 43 or any other suitable component preferably at the lower end of the inner part 17. In the shown embodiment, the securing means 35 is arranged at least primarily between the ring 43 and the container 3. However, other constructional solutions are possible.

FIG. 11 illustrates in a perspective view the container 3 and the associated securing means 35 in the delivery state. In the shown second embodiment, the securing means 35 forms an arrangement of multiple holding elements 36 which are preferably finger-like or leaf-like. The holding elements 36 are annularly arranged around a circumference of the container 3 and/or connected with a ring portion 44 of the securing means 35. In particular, the holding elements 36 are connected with the inner edge of the ring portion 44 and extend axially upwardly, i.e. in the direction of insertion of the container or into the nebulizer 1. The holding elements 36 are biased against the container 3 and/or inclined radially inwardly against the container 3.

The securing means 35 or securing ring formed by the ring portion 44 and the associated holding elements 36 in the shown embodiment comprises preferably fixing portions 40 for fixing the securing means 35 or securing ring at the nebulizer 1, its housing or inner part 17, in particular at the ring 43 counter-bearing the drive spring 7. The fixing portions 40 extend preferably in axial direction from the ring portion 44 and are angled radially outwardly at its free ends so that a form-fit engagement is possible with ring 43 (ring 43 is axially held between the ring portion 44 and the free ends of the fixing portions 40 in the preferred embodiment). Thus, the securing means 35 or securing ring can be securely fixed at the ring 43. However, other constructional solutions are possible as well.

It has to be noted that the securing means 35 or securing ring comprises or consists of a metal and/or stamping part and/or a single unitary part as already described with respect to the first embodiment.

The holding elements 36 of the securing means 35 or securing ring cooperate preferably with engagement means formed on or by the container 3 such that the container 3 is moveable back and forth but is inseparable from the housing or nebulizer 1, and/or such that the transportation lock 29 is formed and/or that the container 3 is (axially) unmoveably held in the delivery state of the nebulizer 1.

In the shown embodiment, the container 3 comprises at least one, here two radial shoulders, protrusions or corrugations 45 as engagement means. The corrugations 45 form preferably ring-like ribs or the like on the outer periphery of the container 3 and/or are axially spaced, in particular such that the holding elements 36 can engage in between the corrugations 45.

The engagement means or corrugations 45 are preferably arranged or formed on the container 3 such that the holding elements 36 engage—in particular in between the two corrugations 45 as schematically shown in FIGS. 10 and 11—in the delivery state such that the container 3 is held axially to avoid complete insertion of the container 3 and/or undesired opening of the container 3 or its first closure 25.

In particular, the upper corrugation 45 prevents that the container 3 can be detached from the nebulizer 1 because the holding elements 36 can not overcome or move over this corrugation 45. Thus, the securing means 35 prevent replacement of the container 3 at all.

In the opposite direction, the lower corrugation 45 forms an obstacle or resistance for the holding elements 36 so that the container 3 is secured against further insertion in the delivery state, i.e. this corrugation 45 forms together with the securing means 35 or its holding elements 36 the transportation lock 29). However, this obstacle or resistance can be overcome, i.e. the transportation lock 29 can be opened, by a sufficiently high force, e.g. by manually closing the housing or manually inserting the container 3, because the holding element 36 can flex radially outwardly so that the lower corrugation 45 can pass and the container 3 can be inserted further, i.e. can move upwardly in FIG. 10.

The corrugations 45 can differ in axial or circumferential location, form, radial extension, inclination, dimension or the like as required or desired, in particular to realize a secure holding of the container 3 in the delivery state, wherein the force is not too high which has to be overcome when the container 3 is further inserted and opened.

FIG. 12 shows the situation with the fully inserted container 3, i.e. the nebulizer 1 in the activated state (with opened transportation lock 29) with completely opened container 3. The container 3 is connected with holder 6. The drive spring 7 is not tensioned, i.e. the FIG. 12 shows the nebulizer in the non-tensioned state.

FIG. 13 shows a partial enlargement of the FIG. 12 in the area of the securing means 35. In this state, the container 3 can move essentially freely relative to the securing means 35 axially back and forth during the use of the nebulizer 2. However, the holding elements 36 will engage with the engagement means, here first with the lower corrugation 45, when it is tried to separate a container 3 from the nebulizer 1. The two corrugations 45 provide double security against separatation of the container 3 after it has been inserted completely or after the securing means 35 or holding elements 36 have passed the lower corrugation 45.

Generally, it should be pointed out that in the proposed nebulizer 1 the container 3 can preferably be inserted, in the nebulizer 1. Consequently, the container 3 is preferably a separate component. However, the container 3 may theoretically be formed directly by the nebulizer 1 or part of the nebulizer 1 or may otherwise be integrated in the nebulizer 1.

As already mentioned, individual features, aspects and/or principles of the embodiments described may also be combined with one another as desired and may be used particularly in the nebulizer according to FIGS. 1 and 5 but also in similar or different nebulizers.

Unlike freestanding equipment or the like the proposed nebulizer 1 is preferably designed to be portable and in particular is a mobile hand operated device.

The proposed solution may, however, be used not only in the nebulizers 1 specifically described here but also in other nebulizers or inhalers, e.g. powder inhalers or so-called metered dose inhalers.

Preferably, the fluid 2 is a liquid, as already mentioned, especially an aqueous pharmaceutical formulation. However, it may also be some other pharmaceutical formulation, a suspension or the like.

According to an alternative embodiment the fluid 2 may also comprise particles or powder. In this case, instead of the expulsion nozzle 12, some other kind of supply device may be provided, especially an expulsion opening (not shown) or a supply channel (not shown) for supplying the fluid to or powder or the like into the mouthpiece 13. The optional air supply opening 15 then serves to supply ambient air preferably in parallel so as to general or allow an airflow with a sufficient volume for breathing in or inhaling through the mouthpiece 13.

If necessary the fluid 2 may also be atomized by means of a propellant gas.

Preferred ingredients and/or formulations of the preferably medicinal fluid 2 are listed in particular in WO 2009/047173 A2 which is incorporated herewith by reference. As already stated, these may be aqueous or non-aqueous solutions, mixtures, formulations containing ethanol or free from solvent, or the like.

LIST OF REFERENCE NUMERALS

1 nebulizer
2 fluid
3 container
4 bag
5 pressure generator
6 holder
7 drive spring
8 locking element
9 conveying tube
10 non-return valve
11 pressure chamber
12 nozzle
13 mouthpiece
14 aerosol
15 air supply opening
16 upper housing part
17 inner part
17a upper part of the inner part
17b lower part of the inner part
18 housing part (lower part)
19 retaining element
20 spring
21 container base
22 piercing element
23 monitoring device
24 fluid outlet
25 first closure
26 second closure
27 closure part
28 flange
29 transportation lock
30 securing member
31 latching lug
32 latching recess
33 latching arm
34 venting hole
35 securing means
36 holding element
36a end portion
37 locking element
37a end portion
37b actuation portion
38 base
39 spring portion
40 fixing portion
41 edge
42 control member
43 ring
44 ring portion
45 corrugation

What is claimed is:

1. A nebulizer for dispensing a fluid, comprising:
a first housing part;
a second housing part releasably coupled to the first housing part in a longitudinal orientation and direction;
a nozzle;
a container containing the fluid and including a closure part having a first end located within the container and extending toward a second end at which a fluid outlet for the fluid is located, the fluid outlet being closed by a first closure located at the first end of the closure part in a delivery state of the nebulizer;
a conveying element for conveying the fluid from the container through the closure part and the fluid outlet towards the nozzle; and
a securing mechanism formed of metal and fixed to the second housing part, where the securing mechanism operates in the delivery state of the nebulizer and an activated state of the nebulizer, and where in the activated state the securing mechanism operates such that: (i) the container is inseparable from the securing mechanism and thereby inseparable from the second housing part even when the first and second housing parts are separated, and (ii) the container is movable in the longitudinal direction within the securing mechanism, wherein:

the delivery state: (i) is a state in which an end of the conveying element is disposed through the second end and within the closure part and through the fluid outlet of the container, but not piercing the first closure at the first end of the closure part, and (ii) is a state in which the nebulizer is shipped or delivered to the user, and the activated state is a state in which the end of the conveying element advances through the first closure and into communication with the fluid within the container such that the first closure and the fluid outlet are opened inside the nebulizer before or during first use of the nebulizer.

2. The nebulizer according to claim 1, wherein the securing mechanism forms a cage about at least a portion of the container.

3. The nebulizer according to claim 1, wherein the securing mechanism forms a transportation lock for holding the container unmovable in the second housing part in the delivery state of the nebulizer, wherein the transportation lock is openable to place the securing mechanism in the activated state so that the container is moveable within the second housing part back and forth in the longitudinal direction.

4. The nebulizer according to claim 3, wherein the securing mechanism comprises a cage having multiple functions.

5. The nebulizer according to claim 1, where in the delivery state of the nebulizer the securing mechanism operates such that the container is immovable within, and inseparable from, the securing mechanism and thereby immovable within, and inseparable from, the second housing part.

6. The nebulizer according to claim 4, wherein the cage encompasses an end or bottom portion of the container.

7. The nebulizer according to claim 1, wherein the securing mechanism comprises at least one of holding and locking elements, wherein the at least one of holding and locking elements include at least one of fingers, arms and claws, and are radially flexible.

8. The nebulizer according to claim 7, wherein the at least one of holding and locking elements extend in the longitudinal direction of the movement of the container.

9. The nebulizer according to claim 7, wherein the at least one of holding and locking elements securing the container in the delivery state are actuatable or flexible by at least one of the first and second housing parts or any other component of the nebulizer.

10. The nebulizer according to claim 1, wherein the securing mechanism comprises an opening means for opening a venting hole of the container.

11. A nebulizer for dispensing a fluid, comprising:
a first housing part;
a second housing part releasably coupled to the first housing part in a longitudinal orientation and direction;
a nozzle;
a container containing the fluid and including a fluid outlet and a closure part having a first end located within the container and extending toward a second end at which the fluid outlet is located, the fluid outlet being closed by a first closure located at the first end of the closure part in a delivery state of the nebulizer;
a conveying element for conveying the fluid from the container through the closure part and the fluid outlet towards the nozzle; and
a securing mechanism formed of metal into a ring arrangement, where the securing mechanism operates in the delivery state of the nebulizer and an activated state of the nebulizer, and where in the activated state the securing mechanism operates such that: (i) the container is inseparable from the securing mechanism and thereby inseparable from the first housing part even when the first and second housing parts are separated, and (ii) the container is movable in the longitudinal direction within the securing mechanism, wherein:

the delivery state: (i) is a state in which an end of the conveying element is disposed through the second end and within the closure part and through the fluid outlet of the container, but not piercing the first closure at the first end of the closure part, and (ii) is a state in which the nebulizer is shipped or delivered to the user, and the activated state is a state in which the end of the conveying element advances through the first closure and into communication with the fluid within the container such that the first closure and the fluid outlet are opened inside the nebulizer before or during first use of the nebulizer.

12. The nebulizer according to claim 1, wherein the first and second housing parts are closed only partly in the delivery state and are completely closed at least one of before and upon using the nebulizer.

13. The nebulizer according to claim 3, wherein the transportation lock is opened automatically when completely closing the first and second housing parts.

14. The nebulizer according to claim 13, wherein the second housing part is inserted partly into the first housing part in the delivery state and which is inserted completely into the first housing part for completely closing the first and second housing parts.

15. The nebulizer according to claim 1, wherein the second housing part and the container, which is inseparable from the second housing part, are replaceable as a set.

16. The nebulizer according to claim 11, wherein the container comprises engagement means and the container is inseparable from the nebulizer due to an engagement of holding elements of the securing mechanism with the engagement means of the container.

17. The nebulizer according to claim 16, wherein the engagement means of the container comprise at least one of a radial shoulder, a protrusion and a corrugation.

18. The nebulizer according to claim 1, wherein the nebulizer is constructed as an inhaler for medical aerosol treatment.

19. The nebulizer according to claim 16, wherein the holding elements include at least one of fingers, arms and claws, and are radially flexible.

20. The nebulizer according to claim 19, wherein the holding elements extend in the longitudinal direction of insertion of the container into the nebulizer.

21. The nebulizer according to claim 16, wherein the engagement means of the container comprise at least two radial shoulders, protrusions or corrugations and the holding elements engage between the two radial shoulders, protrusions or corrugations.

22. The nebulizer according to claim 21, wherein:
a first of the at least two radial shoulders, protrusions or corrugations, together with at least one of the securing mechanism and the holding elements, prevents the container from being detached from the nebulizer in the delivery state, and
a second of the at least two radial shoulders, protrusions or corrugations forms an obstacle or resistance for the holding elements against further insertion of the container in the delivery state.

* * * * *